(12) United States Patent
Clarke et al.

(10) Patent No.: US 6,743,632 B2
(45) Date of Patent: Jun. 1, 2004

(54) DIRECTIONAL ACCELERATION VECTOR-DRIVEN DISPLACEMENT OF FLUIDS (DAVD-DOF)

(75) Inventors: Mark S. F. Clarke, League City, TX (US); Daniel L. Feeback, Houston, TX (US)

(73) Assignee: Universities Space Research Association, Columbia, MD (US)

(*) Notice: Subject to any disclaimer, the term of this patent is extended or adjusted under 35 U.S.C. 154(b) by 258 days.

(21) Appl. No.: 09/805,057

(22) Filed: Mar. 14, 2001

(65) Prior Publication Data

US 2002/0142470 A1 Oct. 3, 2002

(51) Int. Cl.⁷ .................... G01N 35/00; G01N 21/00; G01N 31/00; G01N 9/30; B32B 27/04; B01L 9/00; B04B 11/00; B04B 1/04; B04B 1/08

(52) U.S. Cl. ................. 436/45; 436/43; 436/46; 422/63; 422/65; 422/72; 422/104; 494/17; 494/68; 494/37

(58) Field of Search .............. 422/104, 63, 65, 422/72; 436/43, 45, 47, 46; 494/7, 17, 18, 34, 37, 68

(56) References Cited

U.S. PATENT DOCUMENTS

| | | | |
|---|---|---|---|
| 3,352,280 A | | 11/1967 | Hughes et al. |
| 3,901,658 A | * | 8/1975 | Burtis et al. .................. 23/259 |
| 4,092,113 A | * | 5/1978 | Hardy ......................... 436/177 |
| 4,192,250 A | | 3/1980 | Van Duijn |
| 4,225,558 A | | 9/1980 | Peterson et al. |
| 4,236,666 A | * | 12/1980 | Aeschlimann et al. ........ 494/20 |
| 4,612,873 A | | 9/1986 | Eberle |
| 4,883,763 A | * | 11/1989 | Holen et al. .................. 436/45 |
| 5,061,446 A | * | 10/1991 | Guigan ........................ 422/64 |
| 5,089,417 A | * | 2/1992 | Wogoman .................... 436/45 |
| 5,110,552 A | * | 5/1992 | Guigan ........................ 422/64 |
| 5,160,702 A | | 11/1992 | Kopf-Sill |
| 5,173,193 A | | 12/1992 | Schembri |
| 5,286,454 A | | 2/1994 | Nilsson et al. |
| 5,589,400 A | | 12/1996 | Hayes |
| 5,591,643 A | | 1/1997 | Schembri |
| 5,679,154 A | | 10/1997 | Kelly et al. |
| 5,935,858 A | * | 8/1999 | Herst ........................... 436/45 |
| 6,008,009 A | | 12/1999 | Clarke et al. |
| 6,143,247 A | * | 11/2000 | Sheppard et al. ............. 422/63 |
| 6,153,148 A | * | 11/2000 | Thomas ....................... 422/72 |
| 6,235,531 B1 | * | 5/2001 | Kopf-Sill et al. ............. 436/45 |
| 6,319,469 B1 | * | 11/2001 | Mian et al. ................... 422/64 |
| 6,391,264 B2 | * | 5/2002 | Hammer et al. .............. 422/72 |
| 2002/0048533 A1 | * | 4/2002 | Harms et al. ................. 422/99 |
| 2002/0064885 A1 | * | 5/2002 | Bedingham et al. ......... 436/174 |
| 2002/0187072 A1 | * | 12/2002 | Karp ............................ 422/60 |
| 2003/0036206 A1 | * | 2/2003 | Chien et al. ................. 436/180 |

* cited by examiner

*Primary Examiner*—Jill Warden
*Assistant Examiner*—Brian R. Gordon
(74) *Attorney, Agent, or Firm*—J. Gibson Semmes, Esq.

(57) ABSTRACT

Centrifugal analyzer and method for staining biological or non-biological samples in microgravity, wherein the method utilizes an increase in weight of a fluid sample as a function of g-load, to overcome cohesive and frictional forces from preventing its movement in a preselected direction. Apparatus is characterized by plural specimen reservoirs and channels in a slide, each channel being of differing cross-section, wherein respective samples are selectively dispensed, from the reservoirs in response to an imposed g-factor, precedent to sample staining. Within the method, one thus employs microscope slides which define channels, each being of a differing cross-section dimension relative to others. In combination therewith, centrifugal slide mounting apparatus controllably imposes g-vectors of differing magnitudes within a defined structure of the centrifuge such as a chip array.

24 Claims, 8 Drawing Sheets

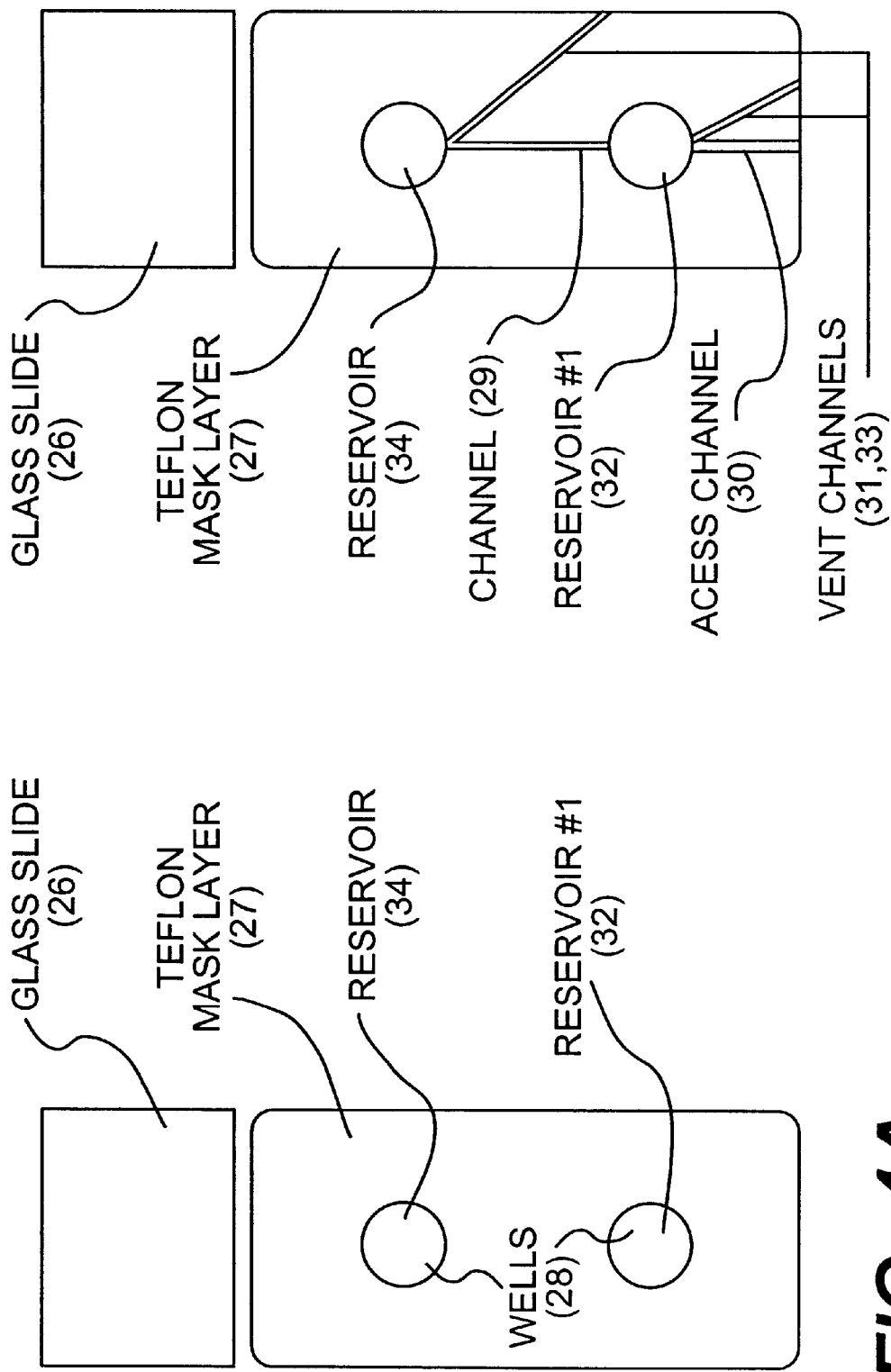

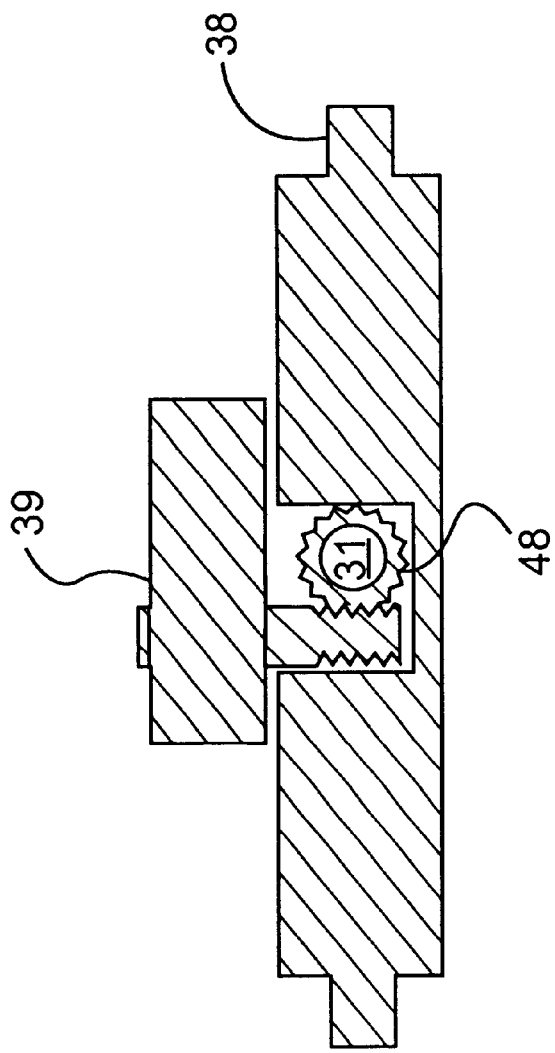
FIG. 5C (CUTAWAY)

DIRECTIONAL ACCELERATION VECTOR-DRIVEN DISPLACEMENT OF FLUIDS (DAVD-DOF)

RELATED APPLICATIONS

U.S. Pat. No. 6,008,009 CENTRIFUGE-OPERATED SPECIMEN STAINING METHOD AND APPARATUS, Dated Dec. 28, 1999, Inventors Mark S. F. Clarke and Daniel L. Feeback.

U.S. DISCLOSURE DOCUMENT NO. 470956, RECORDED UNITED STATES PATENT AND TRADEMARK OFFICE Mar. 16, 2000, Authors Mark S. F. Clarke and Daniel L. Feeback.

U.S. GOVERNMENT RIGHTS

This invention was made with U.S. Government support under contract NCC9-41 awarded by NASA. The Government has certain rights in this invention.

BACKGROUND OF INVENTION

In the past, the inventors herein have patented a device for the staining of biological samples in microgravity aboard a spacecraft, known as the centrifuge operated slide stainer. This device and technology was developed in response to the need for real-time analysis of crew member blood samples and microbiological monitoring of samples obtained from the environmental systems of a spacecraft. That method and associated apparatus, hereinafter COSS, appear in U.S. Pat. No. 6,008,009, dated Dec. 28, 1999, entitled Centrifuge-Operated Specimen Staining Method and Apparatus, inventors Mark S. F. Clarke and Daniel L. Feeback. Further study of the need for analysis of biological samples during space flight suggested that a greater range of sample types and staining protocols would have to be accommodated by any staining technology selected for flight. This was due not only for medical operations reasons and environmental monitoring, but also for the anticipated increased requirement for analysis of biological samples obtained from science experiments conducted aboard the established International Space Station. In order to accommodate such an increase in demand, the possibility of miniaturizing the COSS technology was investigated so that a greater range of samples and staining protocols could be accommodated with no, or less, impact on crew time, solid waste production and upmass than that of the aforesaid technology. The need for real-time analysis of biological samples during space flight is exemplified by the requirement for a differential white cell count DWCC, a critical medical diagnostic tool which can be used to distinguish between various conditions that induce alterations in the total number and type of white blood cells produced by the human body. For example, a DWCC can be used to distinguish between bacterial or viral infections, in the differential diagnosis of an allergic reaction or to detect the presence of myeloproliferative disorders or leukemia. Microgravity exposure during space flight results in hemodynamic changes in crew members, which in turn impacts the production of white blood cells. Heretofore, no data are available to establish the "normal baseline" for white blood cell production in microgravity. Without first knowing the extent to which microgravity exposure impacts white blood cell production, or secondly the proper "microgravity baseline" for a normal healthy crew member in space, it is quite possible that a bacterial or viral infection may be overlooked or misdiagnosed, or that a potentially much more serious problem, such as leukemia, may be attributed to a bacterial or viral infection in a particular crew member. In addition, the requirement for microbiological screening of both medical and environmental samples during space flight, which can only be accomplished by utilizing specific staining techniques for microbe identification, is a second example of the need for real-time analysis capabilities using standard staining techniques on-orbit. At present, it is impossible to perform a DWCC while aboard a space craft. Whole blood smears have been produced in microgravity, but as yet it has remained impossible to perform a DWCC without returning the blood smear to Earth. Due to the limited life span of such smears, it is impossible to make a definitive statement with regard to the effect of microgravity exposure upon white blood cell profiles based on such samples. Until real-time performance and analysis of a DWCC can be achieved aboard the space craft, critical crew health information thus remains unobtainable.

In a terrestrial setting, a differential white cell count is obtained by preparing a blood smear on a glass slide, fixing the cells in the smear to the surface of the slide, staining the cells with a histochemical stain followed by washing the slide in a clean buffer solution prior to viewing under the microscope where a "differential" white blood cell count is made by morphological criteria. The protocol outlined above is a simple and universally used technique to perform a DWCC. However, this technique requires the use of liquid buffer solutions, including fixatives and dye solutions. While this technique is performed easily on Earth, the problems associated with liquid handling in microgravity make such a task nearly impossible. Past attempts at solving this problem have included several "cell stainers" which were tested by NASA or its contractor personnel but have since proved unsuitable for use in microgravity. The first attempt was a slide stainer which flew aboard Sky Lab. This device proved very cumbersome, required large volumes of buffer solutions and had limited use due to precipitate formation in the staining solutions which blocked the intricate tubing arrangement required to apply the staining solutions to the blood smear. A second attempt was based upon an airtight chamber design which contained a blood smear slide, into which buffer solutions and/or staining solutions were introduced using a vacuum system. System operation relied upon a series of one-way and two-way valves in order to achieve an efficient vacuum into which the staining solutions were introduced by hypodermic syringe. The original technology used a hand-held squeeze bulb to create the vacuum which proved inadequate. A later version incorporated mechanical pumps to provide both vacuum production and syringe emptying. The hand-operated version of this technology, although shown to work on the ground and which passed initial testing aboard the KC-135 parabolic aircraft, did not fulfill its potential and has since been shelved as a viable solution to slide staining on-orbit, not least because of its requirement for substantial crew interaction and crew time.

THE PRIOR ART

| INVENTOR | PAT. NO. | DATE | TITLE |
| --- | --- | --- | --- |
| R. Hughes et al. | 3,352,280 | 1967 | Centrifugal Apparatus For Slide Staining |
| van Duijn | 4,192,250 | 1980 | Valve-Centrifuge |
| Peterson et al. | 4,225,558 | 1980 | Fluid sample test apparatus and fluid sample cell for use therein |

-continued

| INVENTOR | PAT. NO. | DATE | TITLE |
|---|---|---|---|
| Eberle | 4,612,873 | 1986 | Centrifuge chamber for cytodiagnostic investigation of epithelial cells contained in a sample |
| Molina et al. | Article* | 1990 | Applied Microbiology Gram Staining Apparatus |
| Kopf-Sill | 5,160,702 | 1992 | Analyzer with improved rotor structure |
| Nilsson et al. | 5,286,454 | 1994 | Cuvette |
| Hayes | 5,589,400 | 1996 | Method of distributing material onto a microscope slide of a large cytology sample chamber |
| Kelley et al. | 5,679,154 | 1997 | Cytology Centrifuge Apparatus |
| Clarke et al. | 6,008,009 | 1999 | Centrifuge-operated specimen staining method and apparatus |

*Applied and Environmental Microbiology, March 1990, p 601–606

SUMMARY OF INVENTION

In the present technology, termed Directional Acceleration Vector-Driven Displacement of Fluids DAVD-DOF the same end point, namely sequential filling and emptying of a staining chamber, is achieved using a network of reservoirs and connecting tubes created on a single slide. However, unlike the earlier COSS technology, fluid displacement is achieved by utilizing the weight of the fluid itself, rather than a weighted plunger, to force the fluid through a network of channels between fluid reservoirs. Selective emptying of separate fluid reservoirs is achieved by altering the cross-sectional area of the channel which connects the reservoirs. As cross-sectional area of the channel decreases, the g-force required to bring about fluid displacement through the channel is increased. This approach reduces the overall size of the equipment required to perform a staining protocol in microgravity as well as reducing the amount of staining reagent required from approximately 3 milliliters per reagent in the original COSS technology to less than 20 microliters in the DAVD-DOF technology. As the staining protocol is carried out in a centrifuge at g-levels above 1× g, the problems associated with liquid handling in microgravity, such as air/liquid mixing and bubble formation do not occur. This is due to the fact that a liquid is much heavier than air in the increased acceleration field produced by its rotation in a centrifuge, thereby producing a clear and defined liquid/air interface, an attribute common to both the original COSS and present DAVD-DOF technologies. The technology described herein is thus based upon the concept that fluids, in this case, staining reagents used for biological sample analysis, can be transferred from one reservoir to another through a connecting tube/channel by applying a gravity vector or acceleration vector in the direction of the required movement. This concept is essentially different from the original COSS device, U.S. Pat. No. 6,008,009. That system utilizes a weighted plunger designed to force fluid from one container to another at a constant level of hypergravity maintained in a standard swing-bucket centrifuge. This arrangement allows the sequential filling and emptying of a staining chamber containing a microscope slide on which a biological sample is mounted. In this centrifugal analysis, the principle of invention is stated as optimizing defined dimensional channels of a specimen slide to effect controlled movement of specimen fluids therein by defined g-forces.

BRIEF DESCRIPTION OF THE DRAWINGS

FIG. 4A a view in elevation of a first test micro-array constructed using a glass layer coated with a teflon mask layer.

FIG. 4B a view in elevation of a second test micro-array constructed using a glass layer coated with a teflon mask layer

FIG. 5C is a cross-sectional view of a mechanism used to actuate movement shown in FIG. 5B.

DESCRIPTION OF PREFERRED EMBODIMENTS

Figure 1:
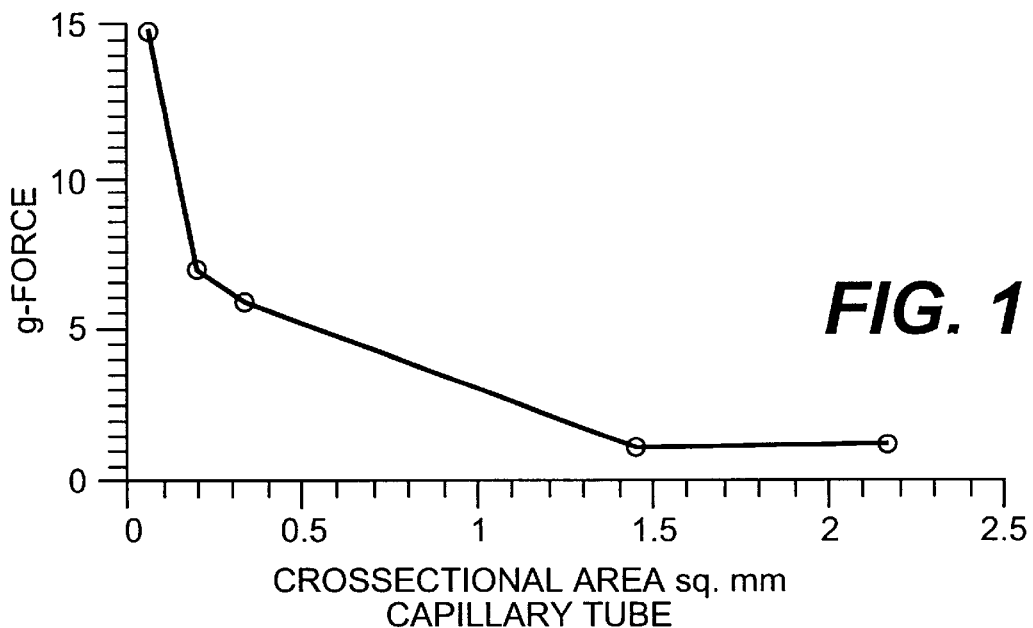
FIG. 1 is a graph of gravitation force required to displace a fluid through a capillary tube versus capillary tube cross-sectional area.

FIG. 1 depicts schematically the G-Force required to displace 50 microliters of fluid down equilength channels of different cross-sectional areas. These values were determined through manual experimentation in which fluid was displaced between two reservoirs connected via a capillary tube (i.e. a hypodermic needles of known cross-sectional area) using a centrifuge to apply hypergravity g-vectors of increasing intensity, in a direction aligned with the length of the capillary tube, to cause fluid displacement. The results of these experiments validate that there exists an inverse relationship between the cross-sectional area of a capillary tube and the g-force which must be applied to cause fluid displacement through the capillary tube. This simple effect, utilizing an increase in weight of a fluid as a function of g-load to overcome the cohesive and frictional forces preventing its movement in a particular direction is the basis of the DAVD-DOF technology, See FIG. 1.

In the experiments, the results of which are summarized in FIG. 1, a reservoir containing 50 microliters of fluid was connected to a second empty reservoir via a hypodermic needle of known cross-sectional area and placed in a centrifuge, with the full reservoir disposed closest to the central spindle of the centrifuge and the capillary tube aligned perpendicularly to the central spindle (i.e., the direction of maximum g-load generated by centrifugal rotation). At 1× g, the surface tension (i.e. cohesive forces of the liquid itself and the frictional forces between the liquid and walls of the reservoir and the needle) prevented the liquid from passing through the needle as a consequence of its own weight. As the RPM of the centrifuge, and hence g-force placed on the liquid was increased, however, the weight of the liquid also increased. When the weight of the liquid was great enough to overcome the forces preventing it from passing down through the needle in the direction of the acceleration vector (i.e. the surface tension of the liquid and the frictional forces between the fluid and the sides of the tube), the liquid was displaced from the full reservoir, through the needle, to the second reservoir. By varying both the internal diameter of the needle and the revolutions per minute (RPM) of the centrifuge and hence g-force on the constant volume of liquid, in this case 50 microliters, the inverse relationship between the cross-sectional area of a capillary tube and the g-force was established. See FIG. 1.

Figure 2B:
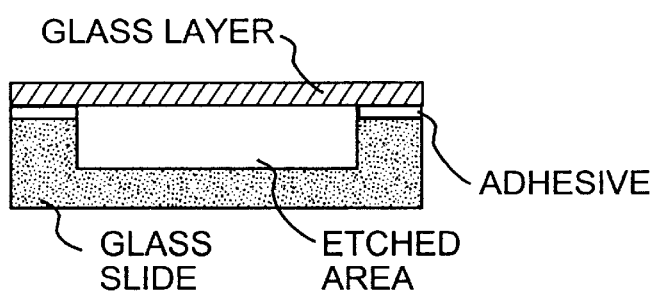
FIG. 2B is a cross-sectional view of a micro-array constructed by adhering a glass layer over an etched glass base.
Figure 2C:
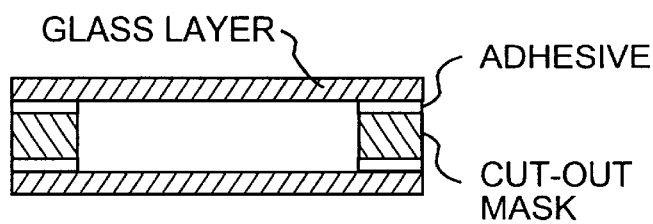
FIG. 2C is a cross-sectional view of a micro-array constructed by sandwiching a cut-out mask between two layers of glass.
Figure 2D:
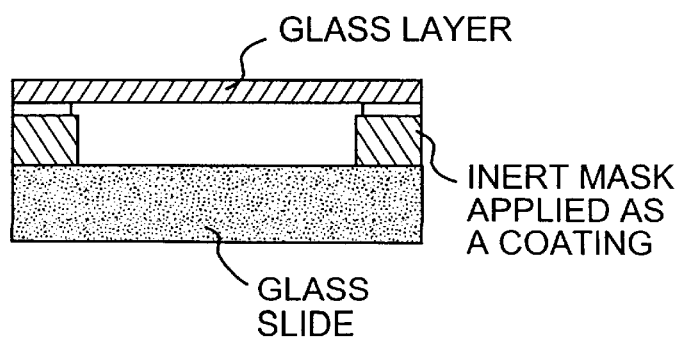
FIG. 2D is a cross-sectional view of a micro-array constructed by adhering a glass layer over an inert mask applied as a coating to a glass base.

To test the concept that the DAVD-DOF principle works at the scale envisioned for creating an array of fluid reservoirs and connecting fluid channels on a microscope slide, microchannels and reservoirs were constructed on a commercially available microscope slide coated with a 10 micron thick Teflon® mask, FIGS. 4A and 4B. The Teflon® mask 27 initially formed a series of wells 28 on the surface of the glass slide 26, FIG. 4A. A 60 micron wide channel 29 was created between the two wells by removing the Teflon® masking material with a razor blade FIG. 4B. An access channel 30 of approximately 1 mm width and a vent channel 31, sixty microns wide, was created in order to load Reservoir 32 with fluid. A similar vent channel 33, sixty microns wide, allows air displacement from Reservoir 34 when fluid is displaced by the DAVD-DOF principle from Reservoir 32. A glass cover-slip was then glued to the surface of the Teflon® mask, to create a device, a typical cross-section of which is presented in FIG. 2D. Using the large access channel 30, reservoir 32 was completely filled with a colored liquid without fluid entering reservoir 34 through the 60 micron thick connecting channel 29. When this slide was then centrifuged at a g-level of approximately 22× g, the colored liquid was displaced from reservoir 32 into reservoir 34 via the connecting 60 micron channel 29.

In the embodiment represented by FIGS. 4A and 4B, channel 29 connecting reservoir 32 to reservoir 34 is approximately 60 microns across and 10 microns deep. The micron sized dimensions of channel 29 are designed to negate the effects of capillary action. At this scale (i.e. the micro-fluidic scale, in which the cross-sectional area of the channel is less than 1000 square microns), the surface tension of the fluid in reservoir 32 at the entrance to channel 29 is the over-riding force, rather than the capillary action forces generated by channel 29. Hence, fluid does not enter channel 29 until additional forces are applied to overcome this surface tension. At higher g-values, however, the weight of the fluid applied in a particular direction overcomes the surface tension effect at the entrance of the channel 29, allowing fluid to enter channel 29 and to flow to reservoir 34. Access channel 30, by contrast, is approximately 1 mm in width and 10 microns deep. Such larger dimensions facilitate the filling of reservoir 32, in part, by capillary action.

Figure 2A:
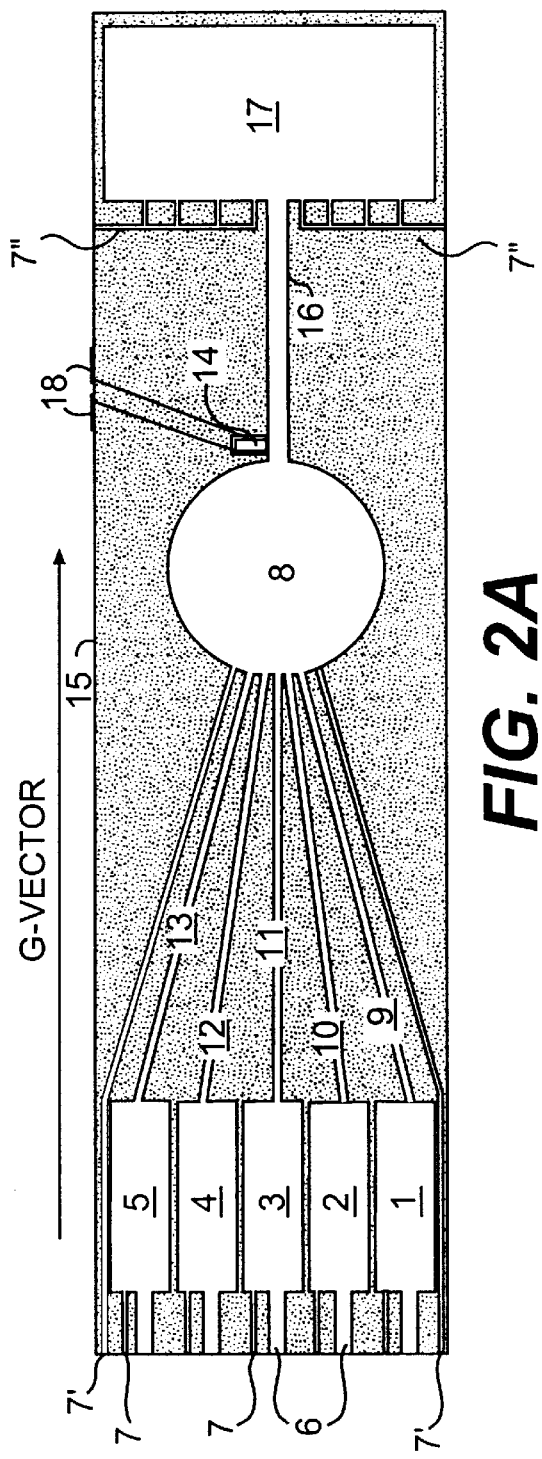
FIG. 2A is a view in elevation of representative micro-array.
Figure 2E:
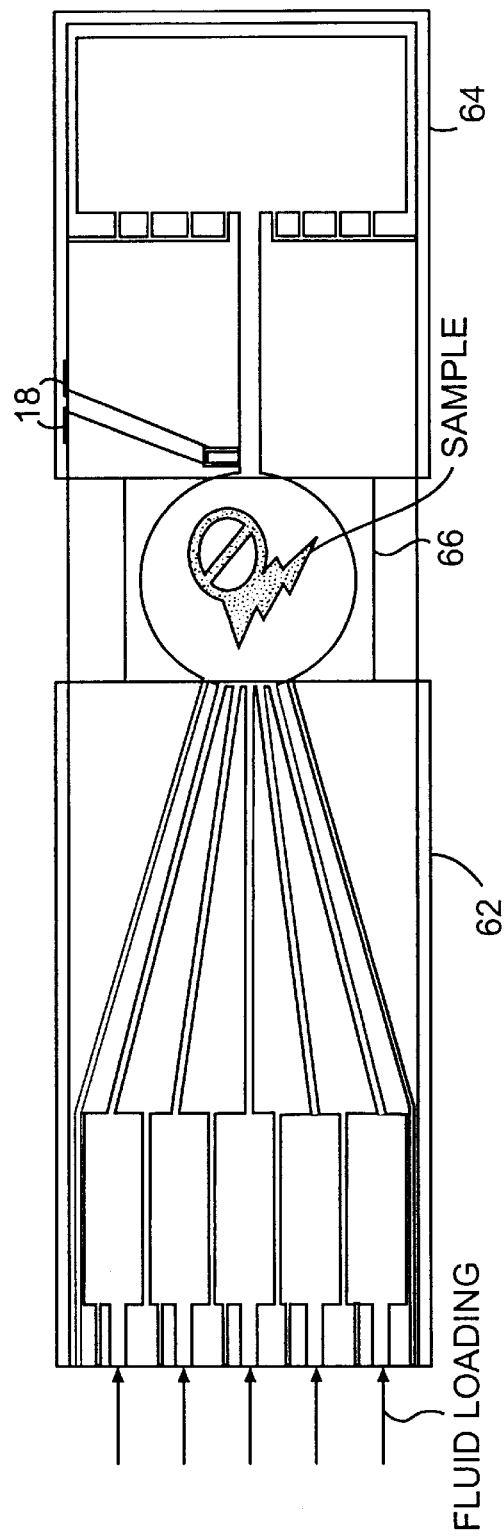
FIG. 2E is the micro-array of FIG. 2A with a fluid sample applied to a staining chamber reservoir.

FIGS. 2A and 2E are diagrammatic representations of an embodiment of a staining apparatus created on a glass microscope slide utilizing the DAVD-DOF principle. A series of fluid reservoirs connected by channels of different cross-sectional dimensions are created on the surface of a glass microscope slide, FIG. 2A. This pattern of interconnected reservoirs and corresponding channels can be created on the slide by either etching of the surface of the glass slide itself and bonding a layer of glass to the etched surface of the slide, FIG. 2B, cutting a mask out of a uniformed thickness sheet of inert material, such as Teflon®, which is then sandwiched and bonded between two layers of glass, FIG. 2C, or etching away of an inert material, such as Teflon® or polycarbonate, previously applied and bonded to the surface of the glass slide as a uniform thickness layer followed by bonding a glass layer to the etched surface, FIG. 2D. Alternatively, the same arrangement can be accomplished by either excimer laser-cutting or photolithography of a predetermined pattern of reservoirs and connecting tubes to create a sheet of inert material of uniform thickness which is then sandwiched and bonded between two layers of glass, FIG. 2C. In FIG. 2E, glass layers 62 and 64 have been bonded to the etched or lithographed surface(s) of the slide using, for example, UV-activated adhesive or electrostatic bonding, thereby creating a sealed array of fluid reservoirs and connecting tubes of defined dimensions with an openfaced staining reservoir 8. Fluid is then dispensed into the fluid reservoirs using a micro-needle and displacement volumetric pipette via their respective access ports 6, displaced air exiting through their respective air vents 7. The sample, e.g. isolated cells, blood smear or tissue section, is first attached onto one surface of a standard 22 mm square glass cover-slip 66 which is then placed sample side down over the staining chamber. The cover-slip is then attached to the surface of the glass slide with air-activated adhesive, such as methyl acrylate, pre-applied to the surface of the slide surrounding the staining chamber. The adhesive is protected from hardening by a gas-impermeable membrane which is removed immediately prior to placement of the cover-slip. This arrangement is the final step in producing a sealed inter-connected array of fluid reservoirs and connecting tubes of different cross-sectional dimensions on the slide.

Figure 3A:
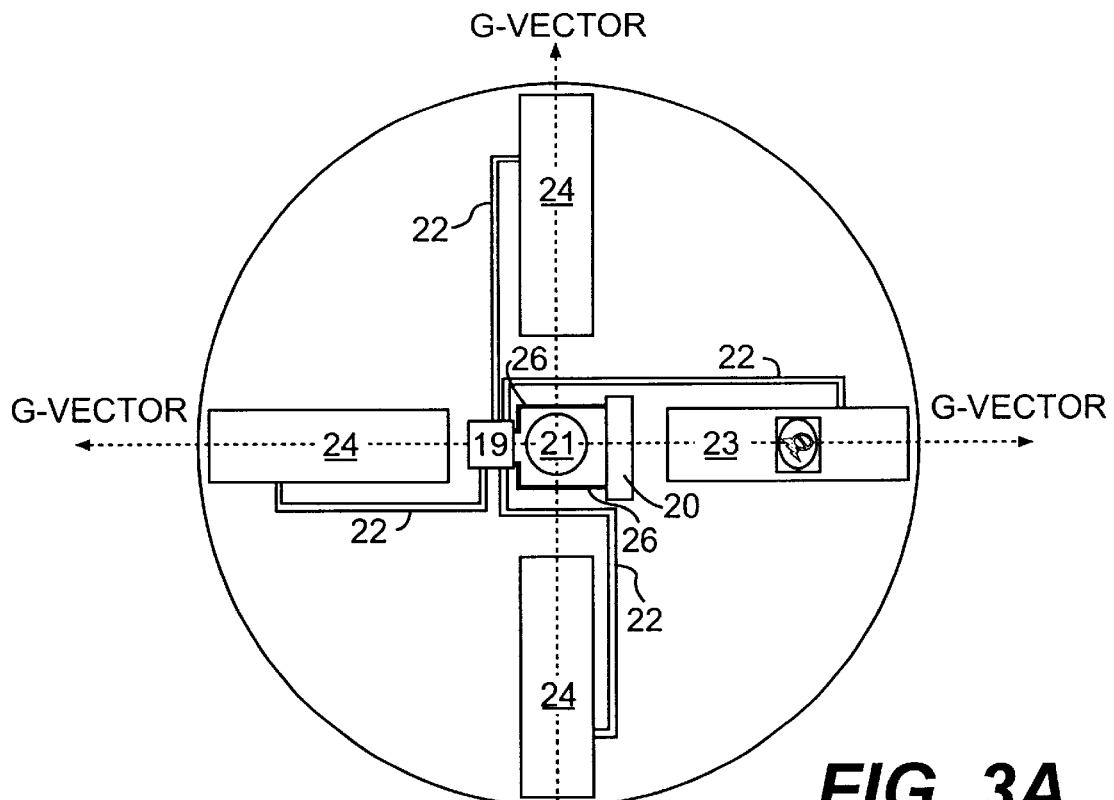
FIG. 3A is a view in elevation of an exemplary embodiment of a spinning disk centrifuge loaded with four micro-arrays.

The slide is then placed on a centrifuge consisting of a flat spinning disc as in plan FIG. 3A. Sequential fluid displacement from the reservoirs, in the depicted configuration all reservoirs contain an equal volume of liquid, into the staining chamber is achieved by incrementally increasing the RPM/g-force produced by the spinning disc centrifuge or SDC.

Where the text and/or figures indicate equal volume of reservoirs and/or equal length of channels, alterations in volumes and/or lengths may be incorporated without derivation from the spirit of this invention.

Principle of Operation:

In FIG. 2A, each fluid reservoir 1, 2, 3, 4 and 5 of slide 15 has an access port 6 through which a known volume of fluid can be dispensed into the reservoir using a microvolumetric displacement pipette. As discussed previously in relation to FIGS. 4A and 4B , the dimensions of access ports 6 are sufficiently large (e.g., approximately 1 mm wide by 10 microns deep) to facilitate the filling of reservoirs 1, 2, 3, 4 and 5, in part, by capillary action. Air displaced from the reservoirs during fluid filling exits via the air vent channels 7. By way of example, a biological sample such as a blood smear or a cell culture is attached to a microscope slide cover-slip, FIG. 2E, and the cover-slip is placed sample-side down, over the top of the staining chamber 8 which has been left uncovered. The cover-slip, with mounted sample downwards, is then bonded to the uncovered area of the etched surface of the slide, as previously described, thereby creating a completely sealed array of reservoirs and connecting channels. When g-force is applied to the slide 15 in the direction indicated in FIG. 2A, fluid tends to move in the direction of the g-vector. As a consequence, fluid will be displaced from the reservoirs 1–5 when the weight of the fluid in each reservoir overcomes the surface tension of the fluid itself and the friction forces between the fluid and the walls of both the reservoir and connecting channels. As G-force increases, sequential emptying of reservoirs 1 through 5 into the staining chamber 8 will occur. For example, if reservoirs 1, 2, 3, 4, and 5 are filled with equal volumes of fluid, reservoir 1 will empty into the staining chamber at the lowest g-force of any of the reservoirs 1–5 as that connecting channel 9, between the reservoir 1 and the staining chamber 8, has the largest cross-sectional area of the channels 9 through 13. As discussed previously in relation to FIGS. 4A and 4B, channels 9, 10, 11, 12, and 13 have cross-sectional area's small enough (i.e., less than 1000 square microns) that liquid movement by capillary action along these channels is prevented by the surface tension of the fluid itself. It is only when a gravitational vector of a high enough g value is orientated along the channel that the surface tension forces at the entrance of the channel are overcome and the liquid is forced through the channel into the reaction chamber.

This principal prevails hereinafter. As fluid displacement occurs under hypergravity conditions, liquid/air mixing is precluded during fluid displacement, due to the large differential between the weight of the fluid and the weight of the air under such hypergravity conditions which ensures a highly discrete air-liquid interface and prevents the formation of gas bubbles that may otherwise produce air locks in the channels and chamber/reservoirs. Furthermore, each reservoir is equipped with vents that allow air to escape as fluid enters the reservoir. These vents prevent the formation of bubbles and air locks in channels due to increased air pressure in the respective reservoirs. In FIG. 2a, for example, staining chamber 8 is vented by vents 7' and the waste reagent reservoir 17 is vented by vents 7". When the g-force required to empty the reservoir 1 is achieved, the centrifuge is slowed to a minimal revolution rate for a pre-determined time in order for the fluid to be in contact with the sample in the staining chamber 8. After this pre-determined period of time, micro-valve 14, supplied with electric current via electric contacts 18 on the side of the slide 15, is opened in channel 16 and the centrifuge is spun up again to a g-force below that required for emptying of reservoir 1. The large cross-sectional area of exhaust channel 16, at least 5 times that of channel 9, ensures a rapid emptying of the staining chamber 8 into the waste reagent reservoir 17 at a relatively low g-force compared to that required for emptying of the fluid reservoirs 1–5. The micro-valve 14 is then closed and g-force is increased until emptying of reservoir 2 is achieved, at which time the g-force is again lowered to a nominal value to allow the fluid to react with the sample in staining chamber 8. After a pre-determined period of time the g-force is again increased; the micro-valve 14 is again opened to allow emptying of staining chamber 8. This cycle is repeated until all five reservoirs have been sequentially emptied into the staining chamber 8 and then collected in the waste reagent reservoir 17, leaving an appropriately treated sample in the staining chamber. As both sides of the staining chamber are made from optical quality glass the sample, contained in its staining chamber can be directly viewed under the microscope as would be a normal microscope slide.

Figure 3B:
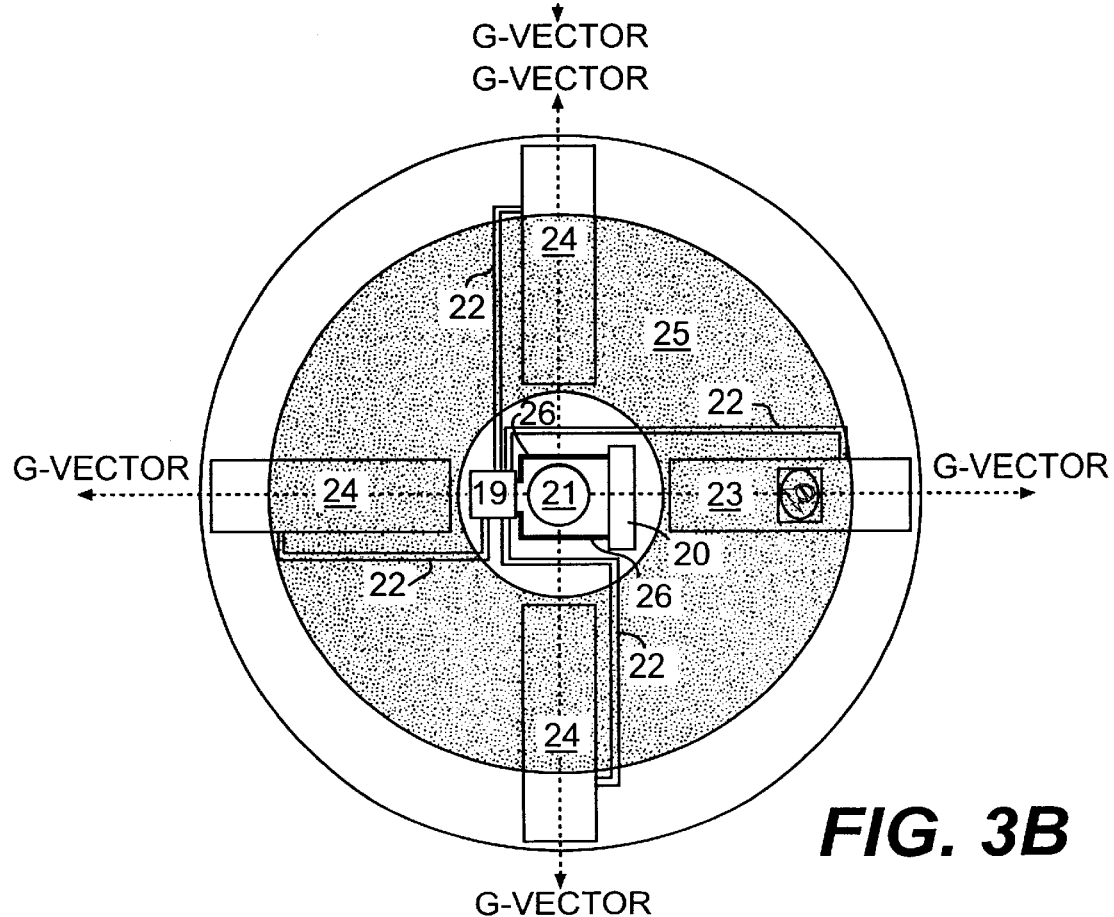
FIG. 3B is a view in elevation of the spinning disk centrifuge of FIG. 3A with a restraining disc mounted over the loaded micro-arrays.

FIGS. 3A and 3B are diagrammatic representations of a first embodiment of the spinning disc centrifuge for use with the DAVD-DOF slide depicted in the schematics of FIGS. 2A–E.

Controllable g-force in a single plane is achieved by using a rotating disc on which the slide 23 is positioned so that the fluid reservoirs on the slide are disposed closest to the central spindle 21 of the centrifuge FIG. 3A. A microprocessor 19 and a power supply 20 for micro-valve operation are housed within the spinning disc nearest the central spindle 21 to reduce any effects of hypergravity upon the electronic components. Power is supplied to microprocessor 19 from power supply 20 via solid state electrodes 26. Power, required for opening and closing of the micro-valve on the slide is supplied to the micro-valve via solid state electrodes 22 emanating from the microprocessor 19. Slides 23 are immobilized in the centrifuge by recesses 24 in the surface of the spinning disc and a restraining disc 25, FIG. 3B, is secured over the central spindle 21, to ensure that the slides are not displaced during centrifugation and that the direction of the g-vector is constant with regard to orientation of the slide. Centrifuge RPM, and hence g-force, is controlled by the microprocessor unit 19 that controls a variable speed electric motor, allowing accurate modulation of g-force by controlling motor RPM. In this fashion, the micro-processor unit communicates with the micro-valve on the slide and the centrifuge motor in order to control the required changes in g-force at the appropriate times during the staining protocol i.e. low rpm when the micro-valve is opened in order to empty the staining chamber; incremental increases in g-force for sequential fluid reservoir emptying when the micro-valve is closed. Although any micro-valve device could be used, one viable micro-valve that has been found suitable operates on the principle of a micro-force array which expands into the connecting channel when an electric current is applied to the array, thereby blocking the channel.

Figure 5A:
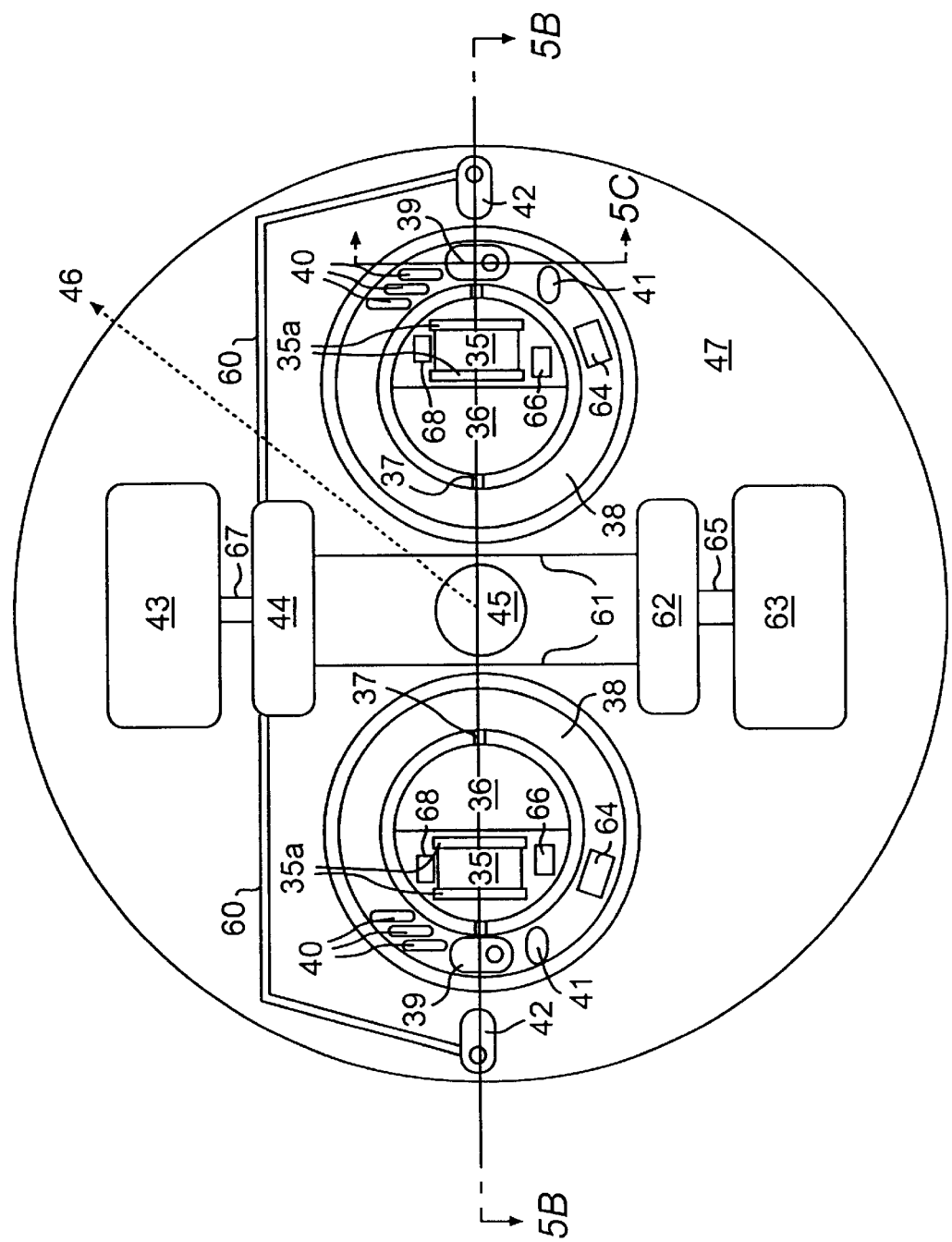
FIG. 5A is a view in elevation of an exemplary embodiment of a spinning disk centrifuge capable of manipulating a micro-array in up to three spatial dimensions relative to an applied g-vector.
Figure 5B:
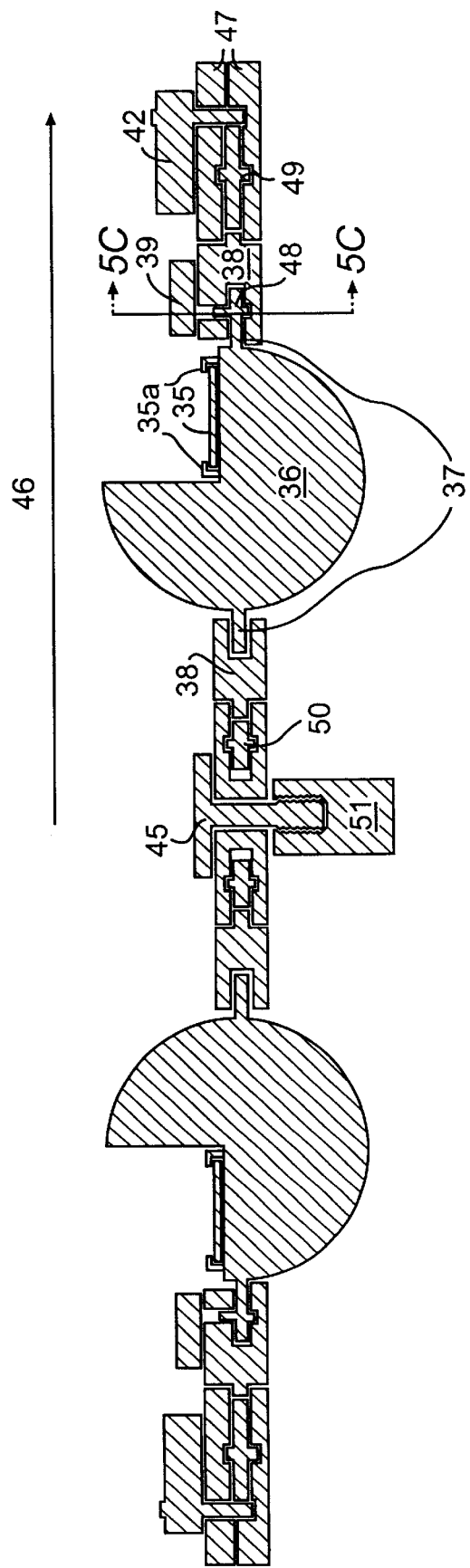
FIG. 5B is a cross-sectional view of the spinning disk centrifuge shown in FIG. 5A.

FIGS. 5A and 5B are diagrammatic representations of a second embodiment of the spinning disc centrifuge for use with a silicon wafer micro-array which utilizes the present DAVD-DOF principle. FIGS. 5A and 5B are described below.

Figure 6:
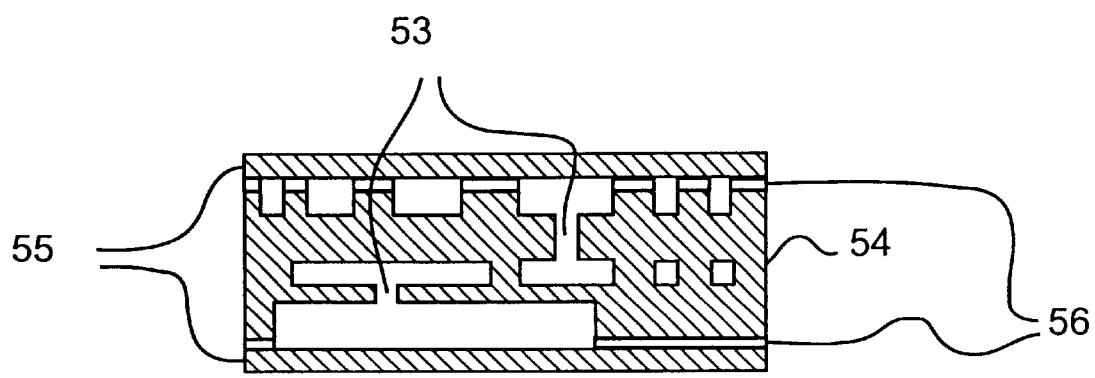
FIG. 6 is a cross-sectional view of a representative three-dimensional micro-array.

A DAVD-DOF microarray 35 is secured in place by clamps 35a attached to a ¾ volume spheroid 36. This spheroid is free to rotate 180 degrees in the vertical plane about a supporting axle 37 attached to a rotating cog-ring 38. Cog ring 38 is free to rotate 360 degrees in the horizontal plane. This composite structure is supported in a spinning disc centrifuge 47 which rotates about central spindle 45 drive shaft 51 assembly, at a predetermined rate to produce a g-vector of a defined level in the direction indicated by the arrow 46. By altering the orientation of the microarray 35 relative to the direction of the g-vector 46, fluid movement between reservoirs can be achieved in three dimensions by aligning the channel connecting said reservoirs to the direction of the g-vector 46. As shown in FIG. 5A and supporting cutaway FIG. 5C, movement of the spheroid 36 in the vertical plane is achieved by activation of a screw drive 39 engaged to an integral cog 48 located on the supporting axle 37. The screw drive is powered by a power supply 40 located on the surface of the rotating cog ring 38 and orientation in the vertical plane is controlled by a programmable microprocessor 41 also located on the surface of the same rotating cog ring 38. By engaging the screw drive with the integral cog 48 on the supporting axle 37 for a predetermined period of time, the orientation of the microarray in the vertical plane can be accurately controlled in one degree increments. The orientation of the microarray 35 relative to the g-vector 46 in the horizontal plane is controlled by a second drive cog 49 and a freely rotating support cog 50 sandwiched between upper and lower layers of the spinning disc centrifuge 47. The drive cog 49 is powered by a second screw drive 42 also located on the upper surface of the spinning disc centrifuge 47. Rotation of the rotating cog ring 38 through 360 degrees in one degree increments is achieved by engaging the screw drive 42 with the drive cog 49 for a predetermined period of time. See FIG. 5B. The drive cog 49, in turn, is engaged to the rotating cog-ring 38 in which the ¾ spheroid 36, upon which the microarray 35 rests, is supported. The screw drive 42 is activated by a power supply 43 and controlled by a programmable microprocessor 44 located on the surface of the spinning disc centrifuge 47. By using a predetermined combination of independent rotational movements of both the rotating cog-ring 38 and the ¾ spheroid 36, the microarray 35 can be placed in any orientation relative to the g-vector 46 in three dimensions. This ability allows connecting channels between fluid reservoirs created on the surface of the microarray 35 to be aligned with the g-vector 46 and hence bring about fluid movement in this direction along the channel. The ability to rotate the microarray in the vertical plane allows a microarray consisting of multiple layers, see FIG. 6, connected by channels 53 between the layers, to be employed. FIG. 6 presents a cross section of a DAD-DOF microarray, such as those presented in FIGS. 2B, 2C, and 2D, in which a 3-dimensional microarray has been created by sandwiching a 3-dimensional inert layer 54, created using photolithography techniques, between two glass layers 55 using and adhesive bond 56. Fluid movement between layers is achieved by rotating the microarray so that the channel connecting the separate layers is aligned to the direction of the g-vector. This has the advantage of allowing the complete volume of the microarray for purposes of sample processing and/or reagent storage rather than some portion on a single surface of the microarray.

As previously discussed in relation to FIGS. 3A and 3B, the spinning disc centrifuge can be equipped with a microprocessor to automate control of centrifuge RPMs and to automate actuation of micro-valves upon each of the respective microarray devices. In the embodiment presented in FIG. 5A, the programmable microprocessor 44 can be used to control the 360 degree rotational positioning of the cog-ring and the 360 degree positioning of the ¾ spheroid, in addition to controlling centrifuge RPMs and micro-valve actuation. Communication between microprocessor 44 and the cog ring screw drive 42 could be accomplished by solid state electrodes 60 mounted upon the spinning disc centrifuge 47. Transmitter/receiver 62 communicates with miniature transmitter/receiver 64, mounted upon the cog-ring, and miniature transmitter/receiver 66, mounted upon the ¾ spheroid, to control positioning of the ¾ spheroid, and actuation of microarray micro-valves, respectively. Transmitter/receiver 62 receives power from power supply 63 via solid state electrodes 65 and is controllable connected to microprocessor 44 by solid state electrodes 61 mounted upon the spinning disc centrifuge 47. Although not indicated in FIG. 5A to avoid congestion within the figure, transmitter/receiver 64 receives power from power supply 40 and is controllably connected to microprocessor 41 by solid state electrodes mounted upon the cog-ring 38. Microprocessor 41 controls actuation of screw drive 39 by solid state electrodes desmounted upon the cog-ring 38, as well. Furthermore, transmitter/receiver 66 receives power from power supply 68 and controls actuation of microarray micro-valves by solid state electrodes mounted upon the ¾ spheroid 36.

The DAVD-DOF technology described here is a preferred means of displacing fluids from one location to another without the production of air bubbles in the solution. As such, this approach overcomes one of the central problems associated with any liquid handling in microgravity, namely air/liquid mixing. In addition, this approach allows the displacement of fluid volumes which at 1× g would form only as a liquid droplet due to surface tension effects. The direct advantage of this technology is that it provides a means of biological or non-biological sample processing, utilizing staining techniques fully validated in terrestrial laboratories, as the staining protocols and liquid reagents utilized with the DAVD-DOF slide apparatus are identical to those used on Earth in reference laboratories. The DAVD-DOF slide technology is small, lightweight, versatile, i.e. any staining protocol, standard or otherwise, may be accommodated by this technology, uses small reagent volumes, produces no solid or liquid waste apart from the slide itself, requires little crew-time for operation and is modular in design. These characteristics, plus the totally automated function of the device once the slide has been placed in the centrifuge, make the DAVD-DOF slide technology very attractive for use aboard ISS for crew health and environmental systems monitoring as well as for scientific research among various scientific disciplines.

The inventors hereby claim:

1. A method of controlling displacement of a fluid from a first reservoir of a plurality of fluid filled reservoirs within a micro-array to a second reservoir within the micro-array, wherein each of said plurality of fluid filled reservoirs is connected to the second reservoir by one of a plurality of interconnecting channels, the method comprising:

applying a centrifugal g-vector to the micro-array; and altering, in at least two spatial dimensions, an orientation of said micro-array relative to the centrifugal g-vector, thereby aligning said interconnecting channel with the centrifugal g-vector.

2. The method of claim 1 wherein orientation of said micro-array relative to the centrifugal g-vector is altered in at least three spatial dimensions.

3. The method of claim 1, further comprising:

controlling displacement of the fluid from the plurality of fluid filled reservoirs to the second reservoir based upon at least one of a volume of the fluid within each of the respective fluid filled reservoirs, a cross-sectional area of the interconnecting channel between each of the plurality of fluid filled reservoirs and the second reservoirs, an alignment of the interconnecting channel relative to the applied centrifugal g-vector and a magnitude of the applied centrifugal g-vector.

4. The method of claim 3 further comprising, increasing the magnitude of the g-vector to overcome a surface tension of the fluid and a frictional force between the fluid and a wall of said interconnecting channel aligned with the applied centrifugal g-vector.

5. The method of claim 3, wherein the cross-sectional areas of the respective connecting channels of the microarray are varied in size, the method further comprising, controlling displacement of fluid from each of the plurality of fluid filled reservoirs into the second reservoir by controlling the magnitude of the applied g-vector.

6. The method of claim 3, further comprising, controlling sequential displacement of fluid from each of the plurality of fluid filled reservoirs by sequentially aligning with the applied g-vector each of the interconnecting channels that connects each of the fluid filled reservoirs to the second reservoir.

7. The method of claim 1 comprising:

controlling displacement of fluid from a first reservoir to a second reservoir by operating a micro-valve to selectively block the channel connecting the first reservoir to the second reservoir.

8. The method of claim 1, wherein the applied g-vector is greater than one times earth's gravitational force.

9. The method of claim 1 wherein the method is performed in a micro-gravity environment.

10. The method of either claim 1 wherein the method further comprises staining a biological fluid sample placed within at least one of said reservoirs.

11. The method of either claim 1 wherein the method further comprises staining a non-biological fluid sample placed within at least one of said reservoirs.

12. A three-dimensional micro-array, for use in real-time centrifugal analysis of samples within a centrifuge capable of altering in at least two spatial dimensions an orientation of the micro-array relative to a centrifugal g-force applied to the micro-array by the centrifuge, the micro-array apparatus therefor comprising:

a plurality of reservoirs; and a plurality of channels, each having a cross-sectional area;

wherein said plurality of reservoirs are interconnected by said plurality of channels;

wherein said plurality of reservoirs and said plurality of channels are positioned within the micro-array in a plurality of layers, said layers connected by at least one interconnecting channel, thereby forming the three-dimensional micro-array;

wherein said centrifuge manipulates the micro-array in at least two dimensions to align an applied g-force with a direction of intended fluid movement within a channel; and wherein at least one of said plurality of reservoirs is configured with an access port channel to receive a fluid loaded into the micro-array.

13. The micro-array of claim 12, further comprising:

an inert layer that contains said three-dimensional network of said plurality of reservoirs and said plurality of channels; and two substantially planar transparent layers, wherein said inert layer is sandwiched between said two substantially planar transparent layers.

14. The micro-array of claim 13, further comprising:

at least one adhesive layer to bond said inert layer to at least one of said planar transparent layers.

15. The micro-array of claim 14, wherein said at least one adhesive layer includes at least one of:

an air activated adhesive;

an ultraviolet light activated adhesive; and an electrostatic bonding adhesive.

16. The micro-array of claim 12, wherein at least one of said plurality of channels has a cross-sectional area less than 1000 square microns.

17. The micro-array of claim 12, wherein said plurality of channels includes:

a first channel with a cross-sectional area less than 1000 square microns; and a second channel that with a cross-sectional area that is greater than the cross-sectional area of said first channel and less than 1000 square microns.

18. The micro-array of claim 12, wherein at least one of said plurality of reservoirs includes a vent channel to vent air displaced by fluid entering said at least one of said plurality of reservoirs.

19. The micro-array of claim 12, wherein at least one of said plurality of channels includes an exhaust channel with a cross-sectional diameter that is at least 5 times that of one of said plurality of channels with the next largest cross-sectional diameter.

20. The micro-array of claim 12, wherein the access port channel is configured with a cross-sectional area greater than 999 square microns.

21. A system for performing real-time centrifugal analysis of fluid samples, the system comprising:

a micro-array containing a plurality of reservoirs and a plurality of interconnecting channels within the micro-array;

means for applying a centrifugal g-vector to the micro-array; and means for altering, in at least two spatial dimensions, an orientation of said micro-array relative to the centrifugal g-vector, thereby aligning at least one interconnecting channel with the centrifugal g-vector.

22. The system of claim 21, wherein said means for altering orientation of said micro-array alters the orientation of said micro-array relative to the centrifugal g-vector in at least three spatial dimensions.

23. The system of claim 21 further comprising, means for increasing the magnitude of the centrifugal g-vector upon aligning an interconnecting channel with the centrifugal g-vector wherein the aligned interconnecting channel has a reduced cross-sectional area relative to a previously aligned interconnecting channel.

24. The system of claim 21 further comprising, means for decreasing the magnitude of the centrifugal g-vector upon aligning an interconnecting channel with the centrifugal g-vector wherein the aligned interconnecting channel has an increased cross-sectional area relative to a previously aligned interconnecting channel.

* * * * *